United States Patent
Rattner et al.

(10) Patent No.: US 6,177,254 B1
(45) Date of Patent: Jan. 23, 2001

(54) NUCLEOLUS AUTOANTIGENIC MARKER FOR SYSTEMIC LUPUS ERTHYEMATOSUS

(76) Inventors: Jerome Bernard Rattner, 35 Point McKay Court, Calgary, Alberta (CA), T3B 5B7; Clark Whitehead, 1894 20$^{th}$St. NW., Rochester, MN (US) 55901

( * ) Notice: Under 35 U.S.C. 154(b), the term of this patent shall be extended for 0 days.

(21) Appl. No.: 09/211,417

(22) Filed: Dec. 15, 1998

(51) Int. Cl.$^7$ .......................... G01N 33/53; C07K 14/00; C07K 16/00; C07K 16/18
(52) U.S. Cl. .......................... 435/7.1; 435/7.72; 435/7.9; 435/7.92; 435/7.93; 530/350; 530/387.1; 530/387.9; 530/388.1
(58) Field of Search .................................... 435/7.1, 7.72, 435/7.9, 7.92, 7.93; 530/350, 387.1, 387.9, 388.1

(56) References Cited

U.S. PATENT DOCUMENTS

| | | |
|---|---|---|
| 4,784,942 | 11/1988 | Harley . |
| 4,812,397 | * 3/1989 | Weisbart . |
| 5,518,881 | 5/1996 | Gordon et al. . |
| 5,700,641 | 12/1997 | Salonen . |

OTHER PUBLICATIONS

Dawson et al, Biochem, Biophys. Res. Comm., vol. 214(1), pp. 152–162, 1995.*
Whitehead et al, Arthritis & Rheum., vol. 39(10), pp. 1635–1642, 1995.*
Whitehead, Clark M., et al.; ASE–1: a novel protein of the fibrillar centres of the nucleolus and nucleolus organizer region of mitotic chromosomes; 1997, Chromosoma 106:493–502.
Adelman JP, Hand CT, Douglas J, Herbert E (1987) Two Mammalian Genes Transcribed from Opposite Strands of The Same Locus, Science 235:1514–1517.
Alderuccio F, Chan EKL, Tan EM (1991) Molecular Characterization of an Autoantigen of PM–Scl in the Polymyosin Scleroderma Overlap Syndrome: A Unique and Complete Human cDNA Encoding an Apparent 75–Kd Acidic Protein of the Nucleolar Complex, J. Exp. Mod. 173:941–951.
Altschul SF, Gish WM, Myers EW, Lipman DI (1990) Basic Local Alignment Search Tool, J. Mol. Biol. 215:403–410.
Chan EK, Imai H, Hamel JC, Tan EM (1991) Human Autoantibody to RNA Polymerase Transcription Factor Hubf. Molecular Identity of Human Nucleolus Organizer Region Autoantigen NOR–90 And Ribosomal RNA Transcription Upstream Binding Factor, J. Exp. Med. 174:1239–1244.
Chen C, Malone T, Beckendorf SK Davis RL (1987) At Least Two Genes Reside Within A Large Intron of the Dwwe Gene of Drosophila, Nature 329:721–724.
Devereux J, Haeberli P, Smithies O (1984) A Comprehensive Set of Sequence Analysis for the VAX, Nucleic Acids Res. 12:387–395.
Dingwall C, Dilworth SM, Black SJ, Kersey SF, Cox LS, Laskey RA (1987) Nucleoplasmin cDNA Sequence Reveals Polyglutamic Acid Tracts and a Cluster of Sequences Homologous to Putative Nuclear Localization Signals, EMBO 160:69–74.
Dundr K, Meier UT, Lewis N. Rekosh D, Harnmarskjold M, Olson MOJ (1997) A Class of Non–Ribosomal Nucleolar Components is Located in the Chromosome Periphery and in NucleolusDerived Foci During Anaphase and Telophase, Chromosoma 105:407–417.
Ftitzler MJ, von Muhlen CA, Toffoli SM, Staub HL, Laxer RM (1995) Autoantibodies; to the Nucleolar Organizer Antigen NOR–90 in Children with Systemic Rheumatic Diseases, J. Rheumatol. 22:521–524.
Ghisolfi L, Joseph G, Amalric F, Emrd M (1992) The Glycine–Rich Domain of Nucleolin has an Unusual Super–Secondary Structure Responsible for its RNA–Helix–Destabilizing Properties, J. Biol. Chem. 267:2955–2959.
Hendzel JB, ML., Furbee CS, Muller MT, Bazett–Jones DP (1996) Topoisomerase II A is Associated with the Mammalian Centromere in a Cell Cycle–and Species–Specific Manner and is Required for Proper Centromere Kinetochore Structure, J. Cell Biol. 134:1097–1107.
Henikoff S, Deene M, Fechtel K, Fristrom L, (1986) Gene within a Gene: Nested Drosophila Genes Encode Unrelated Proteins on Opposite Strands, Cell 44:33–42.

(List continued on next page.)

* cited by examiner

Primary Examiner—Christina Y. Chan
Assistant Examiner—Marianne DiBrino
(74) Attorney, Agent, or Firm—Brown, Pinnisi & Michaels, P.C.

(57) ABSTRACT

A novel nucleolus protein has been identified and cloned using human autoimmune serum. Its cDNA and amino acid sequences have been determined and are disclosed. This antigenic protein, termed ASE-1, has an approximate molecular mass of 55 kDa. Immunoblot analysis indicates that both the native protein and the in vitro translation products of the cDNA migrate on SDS-PAGE at an apparent molecular mass of 90 kDa. Indirect immunofluorescence analysis using antibodies generated to cloned regions of ASE-1 indicates that this protein occurs at the fibrillar centers of the nucleolus in the putative sites of rDNA transcription. During cell division ASE-1 localizes to the nucleolus organizer regions of the chromosomes, where it is closely associated with RNA polymerase 1. As an autoantigenic nucleolar protein, ASE-1 has been found to be a reliable serum marker for systemic lupus erthyematosus (SLE). This finding makes ASE-1 useful in the clinical detection and characterization of the disease. To identify the presence of SLE in an individual patient, a serum samples is taken and screened against the cloned ASE-1 protein to identify sera with anti-ASE-1 autoantibodies. This screening can be done using an ELISA assay, western blot techniques, or by binding the antigen to microspheres and identifying reactive sera by flow cytometry.

3 Claims, 1 Drawing Sheet

OTHER PUBLICATIONS

Lapeyre B, Bourbon K, Amaldric F (1987) Nucleolin, The Major Nucleolar Protein of Growing Eukaryotic Cells, an Unusual Protein Structure Revealed by the Nucleotide Sequence, Proc. Natl. Acad. Sci. USA 94:1472–1776.

Lee WC, Xue Z, Melese T (1991) The NSRI Gene Encodes a Protein that Specifically Binds Nuclear Localization Sequences and has Two RNA Recognition Motifs, J. Cell Biol. 113:1–12.

Martin–Gallardo A, McCombie W.R., Gocayne JD, FitzGerald MG, Wallace S, Lee BMB, Lamerdin J, Kelly JM., Trapp S, Liu L, et al., (1992) Automated DNA Sequencing and Analysis of 106 Kilobases from Human Chromosome 19qi3.3, Nat. Genet. 1:34–39.

McGrath K.E., Smothers J.F., Dadd CA, Madireddi MT, Gorovsky MA, Allis CD (1997) An Abundant Nucleolar Phosphoprotein is Associated with Ribosomal DNA in *Terrahymena Macronuclei*, Mol. Biol. Cell 8:97–108.

Meier UT, Blobel LG (1992) Nopp140 Shuttles on Tracks Between Nucleolus and Cytoplasm, Cell 70:1–20.

Melese T, Xue Z (1995) The Nucleolus, An Organelle Formed by the Act of Building a Ribosome, Curr. Opin. Cell Biol. 7:319–324.

Merino E, Balbas P, Puente JL, Bolivar F (1994) Antisense Overlapping Open Reading frames in Genes from Bacteria to Humans, Nucleic Acids Res. 22:1903–1908.

Monestier M, Nucleolar Autoantibodies in, *Autoantibodies*-(Peter J.B., and Shoenfeld Y. eds.), Elsevier. Amsterdam, pp 567–573 (1996).

Muller MT, Pfund WP, Mehta VB, Trask DK (1985) Eukaryotic Type 1 Topoisomerase Is Enriched In The Nucleolus And Catalytic Ally Active on Ribosomal DNA, EMBO J. 4:1237–1243.

Neqveu A, Marcu KB (1986) Intragenic Pausing and Antisense Transcription Within the Murine c–Myc Locus, EMBO J. 15:2859–2565.

Och R, Lischwe M, O'Leary P, Busch H (1983) Localization of Nucleolar Phosphoproteins B23 and C23 During Mitosis, Exp. Cell Res. 146:139–149.

Ochs RL, Lischwe MA, Spohn WH, Busch H (1985) Fibrillarin: A New Protein of the Nucleolus Identified by Autoimmune Sera, Biol. Cell 54:123–34.

Ochs RL, Stein TW, Chan EKL, Ruutu M, Tan EM (1996) cDNA Cloning and Characterization of a Novel Nucleolar Protein, Mol. Biol. Cell 7:1015–1024.

Reimer G, Rose KM, Scheer U, Tan EM (1987) Autoantibody to RNA Polymerase 1–in Scleroderma Sera, J. Clin Invest 79:65–72.

Roussel P, Andre C, Comai L, Hernandez–Verdun D (1996) The rDNA Transcription, Machinery Is Assembled During Mitosis in Active NORs and Absent In Inactive NORs, J. Cell Biol. 133:235–246.

Scheer U, Weisenberger D (1994) 11e Nucleolus. Curr. Opin. Cell Biol. 6:654–359.

Shan X, Xue Z, Melese T (1994) Yeast NP146 Encodes a Novel Proline Cis–Trans Isomerase that is Located in the Nucleolus, J. Cell Biol. 126:863–862.

Shero JH, Bordwell B, Rothfield NF, Eamshaw WC (1986) High Titers of Autoantibodies to Topoisomerase I (Scl–70) in Sera from Scleroderma Patients, Science 231:737–740.

Spencer CA, Cietz RD, Hodgetts RB (1986) Overlapping Transcription Units in the Dopa Decarboxylase Region of Drosophila, Nature 322:279–281.

Suja JA, Gebrane–Younes J, Geraud G, Hernandez–Verdun D (1997) Relative Distribution of rDNA and Proteins of the RNA Polymerase I Transcription Machinery at Chromosomal NORs, Chromosoma 105:459–469.

Thiry M (1993) Ultrastructural Distribution of DNA and RNA Within the Nucleolus of Human Sertoli Cells as Seen by Molecular Immunocytochemistry, J. Cell Sci. 105:33–39.

Whitehead C.M., Winkfein R.J., Fritzler M.J., and Rattner J.B., (1996) The Spindle Kinesin–Like Protien HsEg5 is an Autoantigen in Systemic Lupus Erythematosus, Arthritis and Rheumatism 39:1635–1642.

Van Duin M, De Wit J, Odlijk K, Westerveld A, Yasui A, Koken MHM, Hoeijmakers IN. Bootsma D (1986) Molecular Characterization of the Human Excision Repair Gene ERCC–1: cDNA Cloning and Amino Acid Homology with the Yeast DNA Repair Gene Radio. Cell 44:913–923.

Van Duin M, Van Den Tol J, Hoeijmakers JHJ, Bootsma D. Rupp IP, Reynolds P, Prakash L, Prakash S (1989) Conserved Pattern of Antisense Overlapping Transcription in we Homologous Human ERCC–1 and Yeast Radio DNA Repair Gene Regions, Mol. Cell Biol. 9:1794–1798.

Viskochil D, Cawthon R, O'Connell P, Xu G, Stevens J, Culver M, Carey I, White R (1991) The Gene Encoding the Oligodendrocyte–Myelin Glycoprotein is Embedded Within the Neurofibromatosis Type I Gene, Mol. Cell Biol. 11:906–912.

NUCLEOLUS AUTOANTIGENIC MARKER FOR SYSTEMIC LUPUS ERTHYEMATOSUS

FIELD OF THE INVENTION

The invention pertains to the discovery of a novel human autoantigen. More particularly, the autoantigen discovered has been sequenced and is useful in the identification of individuals with systemic lupus erthyematosus.

BACKGROUND OF THE INVENTION

Systemic lupus erythematosus (SLE), commonly known as Lupus, is an autoimmune disease characterized by dysregulation of the immune system resulting in the production of antinuclear antibodies, the generation of circulating immune complexes, and the activation of the complement system. The immune complexes build up in the tissues and joints causing inflammation, and degradation to both joints and tissues. While the word "systemic" correctly suggests that the disease effects the entire body and most organ systems, the disease most often involves inflammation and consequent injury to the joints, skin, kidney, brain, the membranes in body cavities, lung, heart, and gastrointestinal tract. An individual with SLE often experiences unpredictable acute episodes or "outbreaks" and equally unexpected remissions. The pathologic hallmark of the disease is recurrent, widespread, and diverse vascular lesions resembling a rash or changes on the surface of the skin.

Physicians have known Lupus since 1828 when it was first described by the French dermatologist, Biett. Early studies were simply descriptions of the disease, with emphasis on the skin rashes typically present in those afflicted with the disease as well as other easily visible symptoms. Forty-five years later a dermatologist named Kaposi noted that some patients with lupus erythematosus (LE) skin lesions showed signs of affected internal organs. In the 1890s, Sir William Osler, a Canadian physician, observed that SLE could affect internal organs without the occurrence of skin changes. In 1948, Dr. Malcolm Hargraves of the Mayo Clinic isolated and described the particular morphology of the LE cell. This cell was found in the blood of patients with SLE. Hargraves' discovery has enabled physicians to identify many more cases of SLE by using a simple blood test. As a result, the number of SLE cases diagnosed has steadily risen.

SLE is not a rare disorder. Although reported in both the extremely old and the extremely young, the disease is chiefly found in women of childbearing age. Among children the occurrence of SLE is three times more likely in females than in males. In the 60% of SLE patients who experience the onset of this disease between puberty and the fourth decade of life, the female to male ratio is 9:1. Thereafter, the female preponderance again falls to that observed in prepubescent children (i.e. 3:1). In addition, the disorder appears to be three times more common in persons of African and Asian descent than in persons of Caucasian descent.

The prevalence of SLE in the United States is an issue of some debate. Estimates of occurrence range from 250,000 to 2,000,000 persons. Problems with identifying SLE are part of the problem in providing estimates of the numbers of individuals affected. The root of this identification problem is the fact that the clinical features of SLE can be mimicked by many other disorders, such as infectious mononucleosis or lymphoma. In this way the actual number of individuals affected is masked.

The etiology of SLE remains unknown. A genetic predisposition, the systemic proliferation of sex hormones, and an environmental trigger likely result in the disordered immune response that typifies the disease. A role for genetics is suggested by the increased percentage of two histocompatibility antigens in patients with SLE, HLA-DR2 and HLA-DR3. In addition, there is an increased frequency of the extended haplotypes HLA-A1, B8, and DR3 in affected individuals. The role for heredity is further supported by the concordance for this illness among monozygotic twins. The polygenic nature, however, of this genetic predisposition as well as the contribution of environmental factors is suggested by the occurrence rate, which is only moderate and reported to be between 25% and 60%.

The body's immune system normally makes proteins called antibodies to protect he body against viruses, bacteria and other foreign materials. These foreign materials are called antigens. In an autoimmune disorder, such as SLE, the immune system loses its ability to tell the difference between antigens and its own cells and tissues. The immune system then makes antibodies directed against "self." These antibodies, called "auto-antibodies," react with the "self autoantigens" to form immune complexes. The immune complexes build up in the tissues, causing inflammation, injury to tissues, and pain.

Since 1954, the various unusual antibodies found to be associated with SLE have been used to study the disease. The above difficulty in identifying the disease, and those afflicted with it, has led to an effort to use the presence of these antibodies as a tool to diagnose the disease. However, the presence of these antibodies may be the result of factors other than SLE, and to date no one autoantibody has been found to be universal to all individuals with SLE.

SUMMARY OF THE INVENTION

Briefly stated, the invention described herein discloses the identification, expression, production, and purification of a novel human protein. Its cDNA and amino acid sequences have been determined and are disclosed. This autoantigenic protein, termed ASE-1, has an approximate molecular mass of 55 kDa and is a component of the nucleolus found in all nucleated human cells. ASE-1 co-localizes with RNA polymerase-I and autoantibodies to ASE-1 are found at a higher frequency in individuals with systemic lupus erthyematosus (SLE). This finding makes ASE-1 a reliable serum marker for SLE, and therefore useful in the detection and characterization of SLE. The cDNA sequences for this nucleolar protein was isolated and then inserted into the pGEX plasmid. The plasmid constructed in this way was then transformed into the E. coli strain JM109 for expression. The E. coli expression vector accurately transcribed and expressed the ASE-1 protein sequence.

Indirect immunofluorescence analysis using polyclonal antibodies generated to cloned and expressed regions of ASE-1 indicate that this protein resides at the fibrillar centers of the nucleolus and the nucleolus organizer regions of mitotic chromosomes during cell division.

To identify the presence of ASE-1 antibodies in an individual patient's serum, a sample is taken and screened against the cloned ASE-1 protein. The presence of the ASE-1 antibody protein complex can be observed through the use of several methods including an ELISA assay, western blot techniques, by binding the autoantigens or specific autoantigenic epitopes to microspheres and identifying reactive sera by flow cytometry, or other known means.

DESCRIPTION OF THE PREFERRED EMBODIMENT

Figure 1:
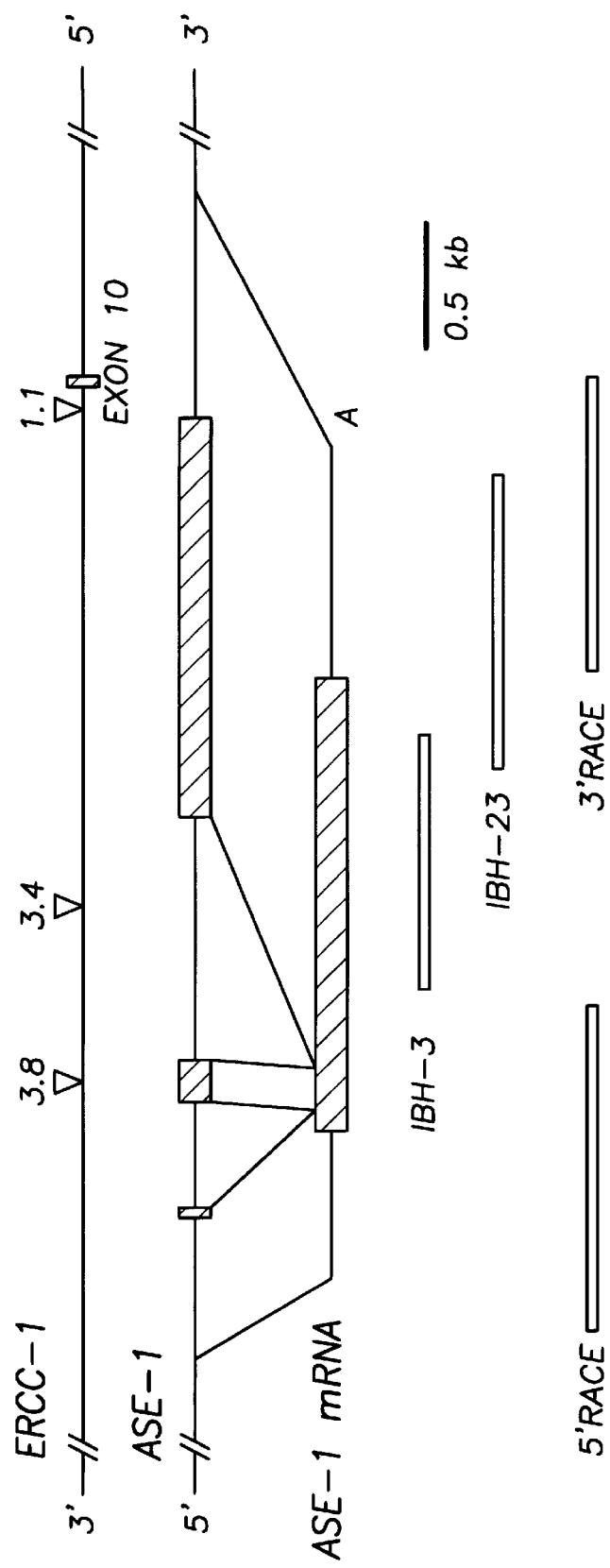
FIG. 1 shows a schematic representation of the genomic organization of the cDNA clones ERCC-1 and ASE-1.

The following abbreviations have designated meanings in the specification:

Abbreviation Key

| | |
|---|---|
| cDNA: | Complementary DNA |
| DFC: | Dense fibrillar components |
| dsDNA: | Double Stranded DNA |
| ERCC-1: | DNA excision and repair enzyme |
| FC: | Fibrillar centers |
| GC: | Granular component |
| GRF: | Glycine-arginine-phenylalanine rich amino acid sequence |
| HLA: | Haplotype |
| IIF: | Indirect Immunofluroescence |
| IPTG: | Isopropyl thiogalactoside |
| LE: | Lupus erythematosus |
| NOR: | Nucleolus organizer regions |
| rDNA: | Ribosomal DNA |
| rRNA: | Ribosomal RNA |
| RRM: | RNA Recognition Motif |
| SLE: | Systemic lupus erythematosus |
| Sm: | Srnith Autoantigens |
| snoRNP: | The small nucleolar ribonucleoprotein |
| TnT: | In vitro transcription and translation |
| UBF/NOR-90 protein: | A rDNA gene-specific RNA polymerase 1 |
| initiation | transcription factor |

The invention discloses the identification and molecular cloning of a novel nucleolar protein, termed ASE-1. Cytological studies indicate that ASE-1 co-localizes with the rDNA throughout the cell cycle. The ASE-1 protein is found within the FCs of the interphase nucleolus and the NOR of mitotic chromosomes. Both of these are sites of rDNA in either a transcriptionally active or inactive state. This localization pattern is unique to the group of nucleolar proteins that are involved with the RNA polymerase-I transcription complex (Dundr et al. 1997; Suja et al. 1997). The transcription complex itself remains assembled on the rDNA promoter site present at the NOR's of mitotic chromosomes during replication. Moreover, interactions between ASE-1 and the UBF/NOR-90 protein, a known member of the RNA polymerase I complex, also delineate the role of ASE-1 within the nucleolus. The UBF/NOR-90 protein is a rDNA gene-specific RNA polymerase 1 transcription initiation factor. This localization confirms the interaction of ASE-1 with the RNA polymerase 1 transcription complex.

Casting and band shift assays were performed in an attempt to define further the function of ASE-1. It has been determined that ASE-1 specifically binds to DNA cellulose. This type of interaction is supported by the presence of a GRF domain in ASE-1. GRF domains have been implicated in mediating interactions with nucleotides.

The addition of ASE-1 to the list of nucleolar proteins that localize to the NORs contributes to a growing appreciation of the complexity of the NOR. It is likely that the presence of nucleolar proteins at the NORs during cell division has a profound effect on the chromatin architecture of this region of the chromosome and provides the basis for its unique constricted nature. The accumulation of ASE-1 and its companion proteins at the NORs likely insures that RNA polymerase 1 transcription can immediately resume upon completion of mitosis.

Human Serum Information

The human sera samples used in this study were obtained from the serum bank of the Advanced Diagnostic Laboratory at the University of Calgary, Canada. Sera were stored either at −20° C. or at −80° C. until required for serological studies. Additional sera were obtained through the Lupus Health Net of Alberta in collaboration with Dr. Steve Edworthy. If collected sera were to used within a short time it was stored at −20° C., while if use of the sera was not planned for several weeks the sera was stored at −80° C.

Cell Culture and Indirect Immunofluorescence

The specificity of autoantibodies for ASE-1 antigens were first detected by indirect immunofluoresence IIF using monolayer cultures of HeLa cells (American Type Tissue Collection, Rockville Md.). The cells were grown on cover slips and fixed for 10 minutes in 3% paraformaldehyde in Dulbecco's phosphate-buffered saline (D-PBS) and permeabilized in 0.5% Triton X-100 in D-PBS. In some experiments, actinomycin D (1 ug/ml) (Sigma, St. Louis Mo.) was added to the cultures for 4 minutes prior to processing. The preparations fixed with paraformaldehyde were briefly washed with D-PBS and incubated for 1 hour at 37° C. with the appropriate serum. Following three washes in D-PBS, the samples were incubated for 1 hour at 37° C. in a fluorescein or C3-conjugated to human, rabbit or mouse IgG (H+L) (Dako Inc., Santa Barbara, Calif.). After incubation, the specimens were washed in D-PBS, counterstained with 4'-6-diamidino-2-phenyl-indole, mounted in 90% glycerol containing P-phenylene-diamine and observed using a Nikon Optoshot fluorescence microscope. Images were recorded on Ilford HP-5 film. Double-label IIF experiments were performed as described above except that two separate incubations of the desired primary and secondary antibodies were used. Digitally computed optical sections were collected.

Isolation of cDNA Clones

Either the prototype ASE-1 human autoimmune serum, designated 11980, or an appropriately immunized rabbit serum, was diluted 1:2000 was used to screen the HeLa cells using the ZAP XR cDNA library (Stratagene, La Jolla, Calif.). Approximately $1 \times 10^6$ recombinant phage were plated on lawns of Escherichia coli BB4 and incubated at 37° C. for 4 hours. Expression of fusion proteins was induced by overlaying with nitrocellulose filters impregnated with isopropyl thiogalactoside (IPTG, Gibco BRL, Burlington, Ontario Canada) for 4 hours. Reactive plaques were detected by processing the filters with an immunoblotting protocol. Positive clones were plaque purified and in vivo excised into a pBluescript plasmid using R408 helper phage (Stratagene, La Jolla, Calif.). The nucleotide sequences of the isolated clones were determined using the dsDNA Cycle Sequencing System (Gibco BRL, Burlington, Ontario Canada). Nucleic acid and protein sequences were analyzed by the University of Wisconsin Genetics Computer Users Group Sequence Analysis Software package Version 8.1 for UNIX computers. Comparisons with known sequences were performed by BLAST on the NCBI Internet Server. The complete 5' sequence of the cDNA was determined by 5' RACE (rapid amplification of cDNA ends) (Whitehead et al. 1996). The 3' end of the cDNA was also determined by RACE using essentially the same protocol except that the dT anchor primer was used rather than oligo (dT) to prime the first-strand of cDNA. The appropriate cDNA sequence-specific primers were designed from the published sequence corresponding to the open reading frame (ORF) of ASE-1 (Van Duin et al. 1989; Martin-Gallardo et al. 1992).

Generation of Fusion Proteins and Antibody Production

All fusion proteins were produced as glutathione-S-transferase (GST) fusions from the pGEX family of vectors (Pharmacia, Baie d'Urfe, Quebec Canada). The first fusion protein (FP-1), encompassing amino acids 20 to 146, was generated by digestion of the 5' RACE product with the endonucleases BstUI and StuI and inserting the resulting DNA fragment into the SmaI site of pGEX 5x-3. To produce FP-2, the 5' overhangs of the Nco1 and EcoR1 fragment (corresponding to amino acids 363 to 488) from clone IBH-23 were filled in with the Klenow fragment of E. coli DNA polymerase 1. The resulting fragment was subloned into the Smal site of pGEX 5x-1 to produce FP-2. To produce FP-3, the cDNA insert from clone IBH-3 was digested with Ncol and the resulting 5' overhang was patched with Klenow fragment and then further digested with EcoR1. The resulting fragment was subcloned into the EcoRI and Sma1 cleavage sites of pGEX 5x-3 to produce FP-3 (corresponding to amino acids 180 to 363). Colonies found to contain inserts were isolated and the insert orientation confirmed by DNA sequencing. Selected clones were grown in 2YT medium to an optical density (OD) of 0.6–0.8 and induced to produce GST fusion proteins by the addition of IPTG to a final concentration of 0.1 mM. Induction was performed for 2 hours at 37° C. The fusion proteins were purified according to the manufacturer's protocol (Pharmacia, Baie d'Urfe, Quebec Canada), suspended in PBS and used to immunize mice and/or rabbits by subcutaneous injection.

The peptide corresponding to amino acids 493 to 506 of the ASE-1 protein (SEQ ID NO:1), was chosen for chemical synthesis (Peptide Synthesis Core Facility, The University of Calgary) owing to its predicted antigenicity. This peptide was coupled to keyhole limpet hemocyanin (KLH) as a hapten, suspended in PBS (phosphate buffered saline), and used to immunize rabbits by subcutaneous injection. The antibody bound to this peptide was designated anti-IBH-KLH.

Immunoprecipitations

Equal volumes of the appropriate TnT reaction were added to NET+F buffer (0.5% NP-40, 150 nM NaCl, 5 mM EDTA, 50 mM TRIS-HCl pH7.4, 0.1% SDS, 0.5% deoxycholic acid, and 0.02% $NaN_3$) for a final volume of 245 ul. Five microliters of the appropriate human autoimmune serum were then added and allowed to incubate with gentle rotation at 4° C. overnight. Protein A-Agarose (Oncogene Science, Homby, Ontario Canada) was added and incubated for 1 hour at 4° C. The immune complexes bound to the agarose were collected by centrifugation at 12,000 g for 1 minute, washed five times in NET+F buffer, boiled in SDS sample buffer for 5 minutes and separated on an 8% SDS-polyacrylamide gel. The gels were fixed in 25% isopropanol, 10% acetic acid for 30 minutes and then soaked in Amplify fluorographic reagent (Amersham, Arlington Heights, Ill.) for an additional 30 minutes. The gels were dried under vacuum and exposed to Kodak Biomax MR film.

Immunoblotting Analysis

Protein samples were re-suspended in SDS-polyacrylamide gel electrophoresis (SDS-PAGE) sample buffer, boiled for 5 min. separated by 10% SDS-PAGE and then electroblotted to nitrocellulose. The nitrocellulose was blocked by incubation in TBS-Tween (25 mM MS-HCl, pH 7.6, 150 mM NaCl, 0.1% Tween-20) containing 3% skin milk for 30 minutes. Strips cut from the filters were then overlaid with the appropriate sera at a dilution of 1:1000 for 1 hour. Unbound antibody was removed by washing the strips three times with TBS-Tween for 10 minutes each. Secondary antibody (horseradish peroxidase-conjugated polyvalent goat anti-human or mouse or rabbit IgG, A, M, 1:2000, (Zymed Laboratories, South San Francisco, Calif.) was incubated with the filters for 30 minutes. Filters were washed three times with TES-Tween for 10 minutes each.

Immuno-reactive bands were visualized by enhanced chemi-luminescence (ECL) according to the manufacturer's protocol (Amersham, Arlington Heights, Ill.)

In Vitro Transcription and Translation

As no cDNA clones were isolated that contained the amino-terminus of ASE-1, a clone was prepared by fusing amino-terminus polymerase chain reaction (PCR) products with a carboxyl-terminus clone (IBH-23). PCR amplification of a first-strand HeLa cDNA was performed using the sense primer SEQ ID No. 3, ACCGCTCGAGATGGAG-GAGCCCCAGGC (containing a XhoI cleavage site near the 5' end and covering the sequence for all amino acids coded for by the first exon and the codon for the first amino acid encoded in the second exon) and the antisense primer SEQ. ID. No. 4, CTTCTTGGTGGATCCCCGAGT (corresponding to bases 1854 to 1875). This PCR product was digested with the endonucleases Xhol and Ncol and cloned into the Xhol/Ncol sites of the plasmid vector pBsKSNco. This plasmid vector has a Ncol site introduced into its EcoRI site ligating in the appropriate oligo-primers. The plasmid produced from this insertion is called pBsXN. The 733 bp Ncol/Xbal fragment isolated from IBH-23 was then subcloned into the Ncol/Xbal sites of pBsXN, resulting in a clone that contained the entire ASE-1 coding region. Plasmid DNA containing the entire ASE-1 coding region was used as a substrate for in vitro transcription and translation assays. T3 RNA polymerase and rabbit reticulocyte lysate contained in the TnT reaction (Promega, Madison, Wis.) were used to incorporate $[^{35}S]$ methionine labeled amino acids, into protein. Negative controls consisted of the rabbit reticulocyte lysate with no DNA template added. The protein products were separated by 8% SDS-PAGE. Gels containing labeled proteins were fixed in 25% isopropanol and 10% acetic acid for 30 minutes and then soaked in Amplify fluorographic reagent (Amersham, Arlington Heights, Ill.) for an additional 30 minutes. The gels were dried under vacuum and exposed to Kodak MR film. Gels containing unlabelled proteins were transferred to nitrocellulose and probed with various antibodies as described above in the immunoblotting protocols.

The Nucleolus

The nucleolus is a complex nuclear component that displays both morphological and functional compartmentalization. Three distinct regions have been identified. The FC's (fibrillar center's) are surrounded by the DFC's (dense fibrillar components), which are in turn encompassed by the GC (granular components). The FCs are thought to be the sites of transcription of rDNA by virtue of the localization of RNA polymerase 1, topoisomerase 1 and the class 1 transcription factor NOR-90/UBF to this region (Fritzler et al. 1995). The surrounding DFC is known to contain the unprocessed nascent rRNA transcripts, mature 28S and 18S rRNA (Scheer and Weisenberger 1994). Partially assembled ribosomal particles 15–20 nm in size can also be visualized in the GC.

ASE-1

Referring to FIG. 1, the identification of nucleolar components has been assisted by the finding that some proteins from each of the nucleolar compartments are autoantigens in certain autoimmune diseases (Monestier 1996). Therefore, component proteins can be used to generate immunoreactive sera against these autoantigenic nucleolus proteins. The reverse is also true, that is, autoimmune sera can be used to identify novel nucleolar proteins, such as with ASE-1. The ASE-1 protein disclosed herein was discovered through the screening of human autoimmune sera reactive against the nucleolus with a human cDNA library. Once isolated and identified, the 55 kDa ASE-1 was sequenced, cloned and used to generate antibodies specific to its epitopic domains.

Previously known human nucleolar autoantigens include fibrillarin, nucleolin, topoisomerase 1, RNA polymerase 1, nucleophosmin/B23, Nopp, and the rDNA gene-specific transcription factor NOR-90/UBF. The NOR-90/UBF autoantigen is localized to the FCs of the nucleolus during interphase and the NORs of the chromosomes during cell division, and migrates as a doublet band around 90 kDa in SDS-PAGE gels. The ASE-1 cDNA sequence encompasses a previously identified open reading frame, which is positioned in an antisense orientation to and overlaps the gene for the DNA excision repair enzyme ERCC-1 (Van Duin et al. 1986). As seen in FIG. 1, the ends of the three known isoforms of ERCC-1 are indicated by the symbol "▼" with the isoform size indicated by solid boxes. The kilobase weights are listed above. Exons are represented by hatched boxes.

ASE-1 has a predicted molecular weight of 55 kDa but migrates at 90 kDa on a SDS-PAGE gel. Evidence shows that this observed migration is due to a feature of the protein sequence itself and is not a result of post-translational modifications. This is more completely demonstrated through the same migration of an unmodified in vitro transription and translation product and the native protein found in HeLa cells. Aberrant migration has been observed for a large number of proteins, particularly those with a high density of charged amino acids. For example, a discrepancy between predicted molecular weight and observed migration on SDS-PAGE is also observed for the 75 kDa PM-Scl autoantigen (Alderuccio et al. 1991). This component, which has a predicted molecular weight of 37 kDa, migrates at 75 kDa and contains a region of charged amino acids in its carboxy-terminus. Many nucleolar proteins with highly charged domains, such as Nopp52, also migrate aberrantly in SDS-PAGE (Spencer et al. 1986). The aberrant migration of ASE-1 is likely due to its ordered arrays of lysine and arginine repeat motifs. The similarity in the cytological distribution and apparent molecular weight between NOR-90/UBF and ASE-1 explains why this nucleolar component has gone undetected in previous studies of autoimmune sera reactive with the nucleolus.

Referring to SEQ. ID. NO. 1, the alternating charge density of ASE-1 and the presence of a putative GRF domain is similar to features found in Nopp52, nucleolin, and NSR-1, all nucleolar proteins identified from a variety of organisms. It is possible that the distribution of these two domains and a third RNA recognition motif (RRM) in Nopp52, nucleolin, and NSR-1 places them in the same family of proteins. In contrast to the features of this family, the GRF in ASE-1 is located in the amino-terminus rather than the carboxyl terminus, while the alternating charge domains are present in the carboxy rather than the amino-terminus. As seen in FIG. 1, characteristic arginine-lysine repeats are underlined and the putative basic regions are represented by peaks above the horizontal axis in the ASE-1 sequence. The GRF domain is shaded. The regions of ASE-1 encompassed by fusion proteins are shown in bold. The amino acid sequence of ASE-1 is represented as SEQ. ID. NO. 1.

Of the human nucleolar proteins that contain one or more of the above-described domains, ASE-1 is the first to localize specifically to the FC and NORs. Nucleolin, which contains a GRF, a RRM and an alternating charge domain similar to that of the ASE-1 protein sequence, is localized to the DFC and GC. The nucleophosmin/B23 protein, which contains an alternating charge domain, is localized to the GC. Fibrillarin, which contains a GRF, is localized to the DFC. Thus, ASE-1 is a distant and distinct relative of the Nopp52 nucleolin and NSR-1 family, and its unique characteristics may have functional correlates associated with its FC localization.

The antisense relationship of the ASE-1 DNA sequence to the ERCC-1 DNA sequence is not unprecedented since such gene arrangements are found in organisms from bacteria to humans. In fact, there is a growing list of genes that contain overlapping reading frames or other embedded transcription units within their sequences. The majority of gene pairs that have overlapping sequences have not been found to be functionally related. This is the case with ASE-1 and ERCC-1, since the functions of a DNA excision repair enzyme (ERCC-1) and a protein localized to the rDNA have no connection.

A large number of autoantigens have been found to contain a distinctive coiled-coil region that frequently contains the epitopes recognized by autoantibodies (Whitehead et al. 1996). ASE-1, in contrast, contains no coiled-coil motif. It is believed that the organized distribution of the lysine and arginine repeats of ASE-1 may produce a three-dimensional configuration that not only alters the electrophoretic mobility of the protein but also enhances its antigenicity. This supposition is supported by the finding that all the clones isolated using the ASE-1 autoimmune serum corresponded to the lysine-and arginine-rich region.

Cytological Localization of ASE-1

The studies using the antibodies raised against the synthetic peptide and the GST fusion proteins FP-2 and 3, which recognize epitopes on three different regions of ASE-1, produce the same cell cycle-specific staining pattern. In interphase cells, ASE-1 is found at discrete foci within the nucleolus. The punctate, nucleolar pattern remains constant through all stages of interphase. No increase or decrease in the number or size of foci between G1, S and G2 is apparent. At the onset of cell division, concurrent with the breakdown of the nuclear architecture and the condensation of chromatin, ASE-1 distribution is enhanced at several distinct regions of the mitotic chromosomes. These distinct regions of reactivity correlate with the nucleolus organizer regions (NORs) as determined by the co-localization of ASE-1 and NOR-90UBF to the identical discrete foci. This pattern persists throughout mitosis until late telophase and early G1-phase of the next cell cycle. By the end of telophase there appears to be an immediate recruitment of ASE-1 to the rapidly reforming nucleoli. This recruitment could utilize either newly synthesized ASE-1 or a pool of soluble ASE-1 present from the preceding cell cycle. Pre-immune sera produced no specific staining pattern (data not shown). This localization pattern is comparable to the pattern reported for another nucleolar autoantigen UBF/NOR-90. The UBF/NOR-90 protein is a rDNA gene-specific RNA polymerase 1 transcription initiation factor.

To determine whether ASE-1 and NOR-90/UBF localize to the same discrete areas of the nucleoli, labeling experiments were performed, these experiments determined that all NOR-90/UBF signals coincided with sites of ASE-1 reactivity. This co-localization is also observed during mitosis, confirming that ASE-1 is a component of the NORs. Further experiments determined that ASE-1, like NOR-90/ UBF, is present in the FCs of interphase nucleoli, the postulated sites of rDNA transcription.

Since ASE-1 is a component of the nucleolus, it is found in most human cells. Further, it is localized to a portion of the nucleolus known as the fibrillar centers, so that the site of its localization can be used to identify and characterize the nucleolus. In fact, antibodies to identify ASE-1 can be used to quantify and characterize nucleoli in both normal cells and malignant or transformed cells.

SLE and Autoantigens

The origin of autoantibody production in SLE is unclear but a role has been suggested for an antigen driven process, spontaneous B-cell hyper-responsiveness, or alternatively impaired immune regulation. Regardless of the etiology of autoantibody production, SLE is associated with the impaired clearance of circulating immune complexes secondary to decreased CRI expression, defective FC receptor function, and deficiencies of early complement components such as C4A.

More is known about the pathogenic cellular and molecular events that are responsible for vascular lesions in SLE than about the origins of autoimmunity. Disease manifestations result from recurrent vascular injury due to immune complex deposition, leukothrombosis, and thrombosis. Additionally, cytotoxic antibodies can mediate autoimmune hemolytic anemia and thrombocytopenia, while antibodies to specific cellular antigens can disrupt cellular function. An example of the latter is the association between anti-neuronal antibodies and neuropsychiatric SLE.

The health status of a patient with SLE is related not only to disease activity, but to the damage that results from recurrent episodes of disease flare (i. e., deforming atrophy, shrinking lung, end stage renal disease, organic mental syndrome, etc.), as well as the adverse effects of treatment (i. e., avascular necrosis of bone, infections, precocious atherosclerosis, etc.).

ASE-1 as a Marker for Systemic Lupus Erthyematosus

A clinical study was carried out with 100 patients diagnosed with SLE and 100 matched control sera. Autoantibody reactivity was studied for the three regions or epitopes that span ASE-1. The results are shown in Table 1 below. These data indicate that ASE-1 has a 47/100 sensitivity for Lupus and a 91/100 specificity for Lupus. It should be noted that in other rheumatic disease groups less than 20% of the sera showed reactivity with ASE-1, and that ASE-1 autoantibodies are not found in individuals without disease. Two common autoantibodies found in the sera of individuals with SLE are to an antigen designated Sm and double-stranded DNA (dsDNA). In the same study group the other current standard marker for Lupus, dsDNA, has a 21/100 sensitivity and a 100/100 specificity. Thus, ASE-1 shows greater sensitivity but slightly less specificity than the standard marker. The data also illustrate that the sensitivity for ASE-1 increases as the number of epitopes recognized by the sera increases. In the patient cohort studied only 2% had antibodies to the Lupus marker Sm. When the clinical information of ASE-1 positive and negative sera were compared, ASE-1 positive individuals were found to have a higher frequency of serositis and photosensitivity. These results indicate that over half of our ASE-1 positive SLE sera did not contain antibodies to either of the major SLE antibody markers, thus making ASE-1 a major and very accurate SLE marker and providing a new method to identify a discrete group of SLE patients.

TABLE 1

Autoantibody Reactivity to Epitopes of ASE-1

| Clinical Cohort 100 control / 100 Lupus | No Reactivity to any Epitope of ASE-1 | Reactivity to 1 Epitope of ASE-1 | Reactivity to 2 Epitopes of ASE-1 | Reactivity to all 3 Epitopes of ASE-1 |
|---|---|---|---|---|
| Control | 57 | 34 | 4 | 5 |
| Lupus | 26 | 27 | 8 | 39 |

Referring to FIG. 1, a BLAST sequence comparison using the cloned cDNA sequence indicates that the cDNA sequence is in an anti-sense orientation to and overlaps the gene of the DNA repair enzyme ERCC-1. ASE-1 was found to contain two domains that are present in a number of nucleolar specific proteins originating from a variety of organisms: (1) a glycine-arginine-and phenylalanine-rich putative nucleotide interact domain and (2) an alternating basic-acidic region. Indirect immunofluorescence analysis using antibodies generated to cloned regions of ASE-1 indicated that this protein occurs at the fibrillar centers of the nucleolus in the putative sites of cDNA transcription. During cell division it is localized to the nucleolus organizer regions of the chromosomes. ASE-1 co-localizes with the RNA polymerase I transcription initiation factor UBF-NOR-90 throughout all stages of the cell cycle. Moreover, it has also been shown that these two proteins associate with each other in vitro. The cDNA sequence is listed below as SEQ. ID. NO. 2.

In Vitro Association of ASE-1 with UBF/NOR-90

The exact co-localization of ASE-1 with UBF/NOR-90 throughout the entire cell cycle and in actinomycin D treated cells led us to investigate whether these two proteins associate or interact with each other. This was accomplished by using the cDNA of ASE-1 and UBF/NOR-90 in in vitro transcription and translation reactions. Two pools of each protein were generated, one labeled with [$^{35}$S] methionine and the other unlabelled. Labeled ASE-1 was mixed with unlabelled UBF/NOR-90 and then immunoprecipitated using a human autoimmune serum that recognized UBF/NOR-90 but not ASE-1. The reciprocal experiment was also performed in which labeled UBF/NOR-90 was mixed with unlabelled ASE-1 and then immunoprecipitated with a human autoimmune serum that recognized ASE-1 but not UBF/NOR-90. Each case showed that there was an interaction between ASE-1 and UBF/NOR-90.

Cloning, Sequencing and Analysis of ASE-1

A human serum, designated 11980, with reactivity to components of the mitotic apparatus as determined by IIF, was used to screen a HeLa cDNA library. One clone, designated IBH-3, was isolated, plaque-purified and sequenced. Its sequence was found to correspond to a 664 base pair region on chromosome 19, antisense to the gene coding for the DNA repair enzyme ERCC-1 (FIG. 1). This region of chromosome 19 had previously been identified as a candidate ORF based on its proximity to a GC island and verification of its transcripts by RNA blot analysis. This ORF was given the designation ASE-1 (Anti-Sense to ERCC-1) by Van Duin et al. (1989) and Martin-Gallardo et al. (1992). Clone IBH3, although within the ORF of ASE-1, contained neither an initiation methionine nor a termination codon. The cDNA library was re-screened with an antibody raised against a synthetic peptide amino acids 493–506 SEQ ID NO:1), C-terminal to IBH-3 but within the potential ORF. An additional clone, IBH-23, was identified. This clone did contain the termination codon and 672 nucleotides of 3' untranslated region (UTR), but had neither a polyadenylation signal nor a poly(A) tail. The full-length ASE-1 transcript was defined by RACE experiments. A graphical representation of the genomic structure of ASE-1 and its relationship to ERCC-1 is shown in FIG. 1. The 3' UTRs of all ERCC-1 mRNA transcripts (1.1, 3.4, and 3.8 KB respectively) overlap the ASE-1 gene.

The transcription of ASE-1 results in an mRNA of 3251 nucleotides (Genbank accession no. U86751). The ASE-1 mRNA has a 5' UTR of 489 and a 3' UTR of 1226 bases with a canonical polyadenylation signal (AATAAA) starting at nucleotide 3235, 17 nucleotides upstream of a poly(A) tail. The ASE-1 gene contains two introns with 89% of the protein being coded by exon 3. The translated portion of this mRNA results in a protein of 516 amino acids with a predicted kDa of 55. A search of the amino acid sequences in the protein databases revealed no significant homology with any known protein. Although an analysis of the amino acid sequence failed to reveal a coiled-coil domain characteristic of many autoantigens, a prominent basic motif of repeated lysine and arginine residues was detected. These repeats average 7 amino acids each and are found at positions: 213–219, 254–262, 290–297, 332–338, 384–395, 427–435, 466–470. These basic repeats, of which none are found in the amino-terminus, are separated by approximately 32 amino acids and contribute to the basic nature of the protein, which has a predicted pH of 8.7. The charge density of ASE-1 demonstrates the organized distribution of these repeats and the fact that each of these basic domains is followed by a small region of opposite, acidic charge. This arrangement of alternating basic/acidic regions has also been described for the nucleolar proteins nucleolin, NSRI, Np146, and Nopp140.

Within ASE-1, starting at amino acid 145, a putative glycine, arginine, and phenylalanine-rich (GRF) region can be found at 9 of 19 amino acid positions, or 47%. A similar concentration of these three amino acids is absent from the region of ASE-1 that contains the alternating basic/acidic motifs. GRF domains, which are found in many nucleolar proteins, are thought to result in a repeated B-turn secondary structure that may be involved in nucleic acid interactions (Ghisolfi et al. 1992). Although no consensus nuclear localization signal sequence was found in ASE-1, one of the repeats has the sequence of amino acids 383–389 of SEQ ID NO:1, which is similar to the nuclear localization signal of the SV-40 large T antigen, except that amino acid residue 387 is R and amino acid residue 389 is V, (Yoneda et al.) 1988).

Molecular Weight Determination

Antibodies raised against the synthetic peptide were used in immunoblots to confirm the molecular weight of ASE-1. When mitotic HeLa cell proteins were probed, a single band at 90 kDa was observed. This is inconsistent with the predicted molecular weight of 55 kDa as calculated from the cDNA nucleotide sequence.

In order to confirm that ASE-1, with a predicted cloned size of 55 kDa, acutally did migrate at 90 kDa, the properties of endogenous ASE-1 from HeLa cells were compared with those from an in vitro transcription and translation assay. Two constructs of the ASE-1 coding sequence were used in these assays. One contained the complete ASE-1 coding sequence and a portion of the 3' UTR and the other had the 3' UTR removed and was linearized at the end of the coding region to ensure that transcription and translation both terminated at the end of our putative ORF. These techniques insured that there was no transcriptional or translational run-on resulting in the production of an incorrect larger-sized protein. Results using both the full-length and 3' UTR deletion construct gave identical results, indicating that transcription and translation both terminated at the correct positions (data not shown). When the resulting in vitro transcription and translation product from our full-length ASE-1 transcript was subjected to a SDS-PAGE the resulting polypeptide had an apparent molecular mass of 90 kDa and was recognized by antibodies raised to two different ASE-1 epitopes. This confirmed the conclusion that our cloned ASE-1 transcript contained the complete gene sequence found in HeLa cells.

Clinical Applications

The finding that ASE-1 is an important SLE serum marker makes it a useful adjunct to current technologies in the laboratory testing for the presence of SLE. Patient serum samples can be screened against the cloned protein to identify sera with anti-ASE-1 autoantibodies. This screening can be done using Western blot techniques, ELISA assays or by binding the antigen to microspheres and identifying reactive sera by flow cytometry. These techniques all allow for a quick and more reliable diagnosis of SLE in patients that might otherwise be diagnosed with another disease presenting similar symptoms. Moreover, the use of ASE-1 as a diagnostic tool also allows the characterization of a distinct SLE afflicted cohort of patients that would not have been otherwise identifiable as SLE positive due to their lack of reactivity towards either Sm or dsDNA.

The production of ASE-1 protein can be scaled for clinical purposes by using known genetic engineering techniques to construct an expression vector such as a plasmid that has had a DNA sequence coding for ASE-1 ligated into it. With the creation of an expression vector carrying the ASE-1 DNA sequence (typically the cDNA sequence), the recombinant plasmid can then be transfected into a variety of host cells. Host cells can range from bacteria to plant or animal cells. Alternatively the ASE-1 sequence can be engineered into other vectors, such as virus, for insertion into a host organism. This host, whether it is a microorganism, virus, plant or animal, is then the product of the gene expression vector. These techniques are useful also in the production of antibodies directed to the ASE-1 sequence specifically.

The creation of antibodies to ASE-1 are potentially useful in developing competition assays for the ASE-1 protein, or for use as a therapeutic agent against SLE. Through the use of an expression vector containing the ASE-1 protein and the consequent production of ASE-1 specific antibodies, known technology allows the development of a hybridoma capable of producing monoclonal antibodies against the ASE-1 protein. These antibodies in turn are useful in competition ELISA protocols, therapeutically against SLE, or as reporter molecules in conjunction with ASE-1 itself.

Literature Cited and Incorporated by Reference:
1. Adelman J P, Hand C T, Douglas J, Herbert E (1987) Two Mammalian Genes Transcribed from Opposite Strands of The Same Locus, Science 235:1514–17.
2. Alderuccio F, Chan EKL, Tan EM (1991) Molecular Characterization of an Autoantigen of PM-Scl in the Polymyosin Scleroderma Overlap Syndrome: A Unique and Complete Human cDNA Encoding an Apparent 75-Kd Acidic Protein of the Nucleolar Complex, *J. Exp. Mod.* 173:941–51.

3. Altschul S F, Gish W M, Myers E W, Lipman D I (1990) Basic Local Alignment Search Tool, J. Mol. Biol. 215:403–410.

4. Chan E K, Imai H, Hamel J C, Tan E M (1991) Human Autoantibody to RNA Polymerase Transcription Factor Hubf. Molecular Identity of Human Nucleolus Organizer Region Autoantigen NOR-90 And Ribosomal RNA Transcription Upstream Binding Factor, J. Exp. Med. 174:1239–44.

5. Chen C, Malone T, Bettendorf S K Davis R L (1987) At Least Two Genes Reside Within a Large Introns of the Dwwe Gene of Drosophila, Nature 329:721–24.

6. Devereux J, Haeberli P, Smithies O (1984) A Comprehensive Set of Sequence Analysis for the VAX, Nucleic Acids Res. 12:387–95.

7. Dingwall C, Dilworth S M, Black S J, Kersey S F, Cox L S, Laskey R A (1987) Nucleoplasmin cDNA Sequence Reveals Polyglutamic Acid Tracts and a Cluster of Sequences Homologous to Putative Nuclear Localization Signals, EMBO 160:69–74.

8. Dundr K, Meier U T, Lewis N, Rekosh D, Harnmarskjold M, Olson M O J (1997) A Class of Non-Ribosomal Nucleolar Components is Located in the Chromosome Periphery and in Nucleolus-Derived Foci During Anaphase and Telophase, *Chromosoma* 105:407–17.

9. Ftitzler M J, von Muhlen C A, Toffoli S M, Staub H L, Laxer R M (1995) Autoantibodies; to the Nucleolar Organizer Antigen NOR-90 in Children with Systemic Rheumatic Diseases, J. Rheumatol. 22:521–24.

10. Ghisolfi L, Joseph G, Amalric F, Emrd M (1992) The Glycine-Rich Domain of Nucleolin has an Unusual Super-Secondary Structure Responsible for its RNA-Helix-Destabilizing Properties, J. Biol. Chem. 267:2955–59.

11. Hendzel J B, M I., Furbee C S, Muller M T, Bazett-Jones D P (1996) Topoisomerase II A is Associated with the Mammalian Centromere in a Cell Cycle- and Species-Specific Manner and is Requiredfor Proper Centromere Kinetochore Structure, J. Cell Biol. 134:1097–1107.

12. Henidoff S, Deene M, Fechtel K, Fristrom L, (1986) Gene within a Gene: Nested Drosophila Genes Encode Unrelated Proteins on Opposite Strands, Cell 44:33–42.

13. Lapeyre B, Bourbon K, Amaldric F (1987) Nucleolin, The Major Nucleolar Protein of Growing Eukaryotic Cells, an Unusual Protein Structure Revealed by the Nucleotide Sequence, Proc. Natl. Acad. Sci. USA 94:1472–76.

14. Lee W C, Xue Z, Melese T (1991) The NSRI Gene Encodes a Protein that Specifically Binds Nuclear Localization Sequences and has Two RNA Recognition Motifs, J. Cell Biol. 113:1–12.

15. Levinson B., Denwrick S, Gamel P, Fisher K, Gitschier 1 (1992) Evidence For a Third Transcript from the Human Factor VIII Gene, Genome 14:585–89.

16. Martin-Gallardo A, McCombie W. R., Gocayne J D, FitzGerald M G, Wallace S, Lee B M B, Lamerdin J, Kelly J M., Trapp S, Liu L, et al. (1992) Automated DNA Sequencing and Analysis of 106 Kilobases from Human Chromosome L9qi3.3, Nat. Genet. 1:34–39.

17. McGrath K. E., Smothers J. F., Dadd C A, Madireddi M T, Gorovsky M A, Allis C D (1997) An Abundant Nucleolar Phosphoprotein is Associated with Ribosomal DNA in Terrahyntena Macronuclei, Mol. Biol. Cell 8:97–108.

18. Meier U T, Blobel L G (1992) Noppl40 Shuttles on Tracks Between Nucleolus and Cytoplasm, Cell 70:1–20.

19. Melese T, Xue Z (1995) The Nucleolus, An Organelle Formed by the Act of Building a Ribosome, Curr. Opin. Cell Biol. 7:319–24.

20. Merino E, Balbas P, Puente J L, Bolivar F (1994) Antisense Overlapping Open Reading frames in Genes from Bacteria to Humans, Nucleic Acids Res. 22:1903–08.

21. Monestier M, Nucleolar Autoantibodies in, *AUTOANTIBODIES* (Peter J. B., and Shoenfeld Y. eds.), Elsevier. Amsterdam, pp 567–573 (1996).

22. Muller M T, Pfund W P, Mehta V B, Trask D K (1985) Eukaryotic Type I Topoisomerase Is Enriched In The Nucleolus And Catalytic Ally Active on Ribosomal DNA, EMBO J. 4:1237–44.

23. Neqveu A, Marcu K B (1986) Intragenic Pausing and Antisense Transcription Within the Murine c-Myc Locus, EMBO J. 15:2859–65.

24. Och R, Lischwe M, O'Leary P, Busch H (1983) Localization of Nucleolar Phosphoproteins B23 and C23 During Mitosis, Exp. Cell Res. 146:139–149.

25. Ochs R L, Lischwe M A, Spohn W H, Busch H (1985) Fibrillarin: A New Protein of the Nucleolus Identified by Autoimmune Sera, Biol. Cell 54:123–33.

26. Ochs R L, Stein T W, Chan E K L, Ruutu M, Tan E M (1996) cDNA Cloning and Characterization ofA Novel Nucleolar Protein, *Mol. Biol. Cell* 7:1015–24.

27. Reimer G, Rose K M, Scheer U, Tan E M (1987) Autoantibody to RNA Polymerase 1-in Scleroderma Sera, J. Clin. Invest 79:65–72.

28. Roussel P, Andre C, Comai L, Hernandez-Verdun D (1996) The rDNA Transcription, Machinery Is Assembled During Mitosis in Active NORs and Absent In Inactive NORs, J. Cell Biol. 133:235–46.

29. Scheer U, Weisenberger D (1994) 11e Nucleolus. Curr. Opin. Cell Biol. 6:354–59.

30. Shan X, Xue Z, Melese T (1994) Yeast NP146 Encodes a Novel Proline Cis-Trans Isomerase that is Located in the Nucleolus, J. Cell Biol. 126:853–62.

31. Shero J H, Bordwell B, Rothfield N F, Eamshaw W C (1986) High Titers of Autoantibodies to Topoisomerase I (Scl-70) in Sera from Scleroderma Patients, Science 231:737–40.

32. Spencer C A, Cietz R D, Hodgetts R B (1986) Overlapping Transcription Units in the Dopa Decarboxylase Region of Drosophila, Nature 322:279–81.

33. Suja J A, Gebrane-Younes J, Geraud G, Hemandez-Verdun D (1997) Relative Distribution of rDNA and Proteins of the RNA Polymerase I Transcription Machinery at Chromosomal NORs, Chromosoma 105:459–69.

34. Thiry M (1993) Ultrastructural Distribution of DNA and RNA Within the Nucleolus of Human Sertoli Cells as Seen by Molecular Immunocytochemistry, J. Cell Sci. 105:33–39.

35. Whitehead C. M., Winkfein R. J., Fritzler M. J., and Rattner J. B., (1996) The Spindle Kinesin-Like Protein HsEg5 is an Autoantigen in Systemic Lupus Erythematosus, Arthritis and Rheumatism 39:1635–42.

36. Van Duin M, De Wit J, Odlijk K, Westerveld A, Yasui A, Koken M H M, Hoeijmakers I N. Bootsma D (1986) Molecular Characterization of the Human Excision Repair Gene ERCC-1: cDNA Cloning and Amino Acid Homology with the Yeast DNA Repair Gene RADIO. Cell 44:913–23.

36. Van Duin M, Van Den Tol J, Hoeijmakers J H J, Bootsma D. Rupp I P, Reynolds P, Prakash L, Prakash S (1989) Conserved Pattern of Antisense Overlapping Transcription in we Homologous Human ERCC-I and Yeast RADIO DNA Repair Gene Regions, Mol. Cell Biol. 9:1794–98.

37. Viskochil D, Cawthon R, O'Connell P, Xu G, Stevens J, Culver M, Carey I, White R (1991) The Gene Encoding the Oligodendrocyte-Myelin Glycoprotein is Embedded Within the Neurofibromatosis Type I Gene, Mol. Cell Biol. 11:906–12.

Accordingly, it is to be understood that the embodiments of the invention herein described are merely illustrative of the application of the principles of the invention. It will be evident from the foregoing description that changes in the form, proportion and construction of the parts of the valve disclosed may be resorted to without departing from the spirit of the invention, or the scope of the appended claims.

What is claimed is:

1. A diagnostic method for detecting systemic lupus erythematosus in humans comprising contacting a serum sample from said humans with an antibody to an ASE-1 protein or polypeptide specific to said humans and said ASE-1 protein or polypeptide so as to detect an elevated level of an autoantibody present in said humans compared to a level of said autoantibody in a normal control, wherein said antibody to said ASE-1 protein or polypeptide has attached to it a label molecule and wherein an elevated level of said autoantibody is indicative of the presence of systematic lupus erythematosus in humans.

2. A diagnostic method according to claim 1, wherein said label molecule is selected form the group consisting of:
   a) a radioactive label;
   b) an enzymatically active label;
   c) a fluorochromatic label;
   d) a dye;
   e) an avidin/biotin label; and
   f) a luminescent label.

3. A diagnostic method according to claim 1, wherein said label molecule is an anti-Ig molecule selected from the group consisting of:
   a) anti-IgG;
   b) anti-IgM;
   c) anti-IgA;
   d) anti-IgD; and
   e) anti-IgE.

* * * * *

SEQUENCE LISTING

<160> NUMBER OF SEQ ID NOS: 4

<210> SEQ ID NO 1
<211> LENGTH: 510
<212> TYPE: PRT
<213> ORGANISM: Homo sapiens
<220> FEATURE:
<223> OTHER INFORMATION: Amino Acid Sequence of ASE-1

<400> SEQUENCE: 1

```
Met Glu Glu Pro Gln Ala Gly Asp Ala Ala Arg Phe Ser Cys Pro Pro
  1               5                  10                  15

Asn Phe Thr Ala Lys Pro Pro Ala Ser Glu Ser Pro Arg Phe Ser Leu
             20                  25                  30

Glu Ala Leu Thr Gly Pro Asp Thr Glu Leu Trp Leu Ile Gln Ala Pro
         35                  40                  45

Ala Asp Phe Ala Pro Glu Cys Phe Asn Gly Arg His Val Pro Leu Ser
     50                  55                  60

Gly Ser Gln Ile Val Lys Gly Lys Leu Ala Gly Lys Arg His Arg Thr
 65                  70                  75                  80

Arg Val Leu Ser Ser Cys Pro Gln Ala Gly Glu Ala Thr Leu Leu Ala
                 85                  90                  95

Pro Ser Thr Glu Ala Gly Gly Gly Leu Thr Cys Ala Ser Ala Pro Gln
            100                 105                 110

Gly Thr Leu Arg Ile Leu Glu Gly Pro Gln Gln Ser Leu Ser Gly Ser
            115                 120                 125

Pro Leu Gln Pro Ile Pro Ala Ser Pro Pro Gln Ile Pro Pro Gly
            130                 135                 140

Leu Arg Pro Arg Phe Cys Ala Phe Gly Gly Asn Pro Pro Val Thr Gly
145                 150                 155                 160

Pro Arg Ser Ala Leu Ala Pro Asn Leu Leu Thr Ser Gly Lys Lys Lys
                165                 170                 175

Lys Glu Met Gln Val Thr Glu Ala Pro Val Thr Gln Glu Ala Val Asn
            180                 185                 190

Gly His Gly Ala Leu Glu Val Asp Met Ala Leu Gly Ser Pro Glu Met
            195                 200                 205

Asp Val Arg Lys Lys Lys Lys Lys Asn Gln Gln Leu Lys Glu Pro
    210                 215                 220

Glu Ala Ala Gly Pro Val Gly Thr Glu Pro Thr Val Glu Thr Leu Glu
225                 230                 235                 240

Pro Leu Gly Val Leu Phe Pro Ser Thr Thr Lys Lys Arg Lys Lys Pro
                245                 250                 255

Lys Gly Lys Glu Thr Phe Glu Pro Glu Asp Lys Thr Val Lys Gln Glu
            260                 265                 270

Gln Ile Asn Thr Glu Pro Leu Glu Asp Thr Val Leu Ser Pro Thr Lys
            275                 280                 285

Lys Arg Lys Arg Gln Lys Gly Thr Glu Gly Met Glu Pro Glu Glu Gly
            290                 295                 300

Val Thr Val Glu Ser Gln Pro Gln Val Lys Val Glu Pro Leu Glu Glu
305                 310                 315                 320

Ala Ile Pro Leu Pro Pro Thr Lys Lys Arg Lys Lys Glu Lys Gly Gln
```

-continued

```
                      325                 330                 335
Met Ala Met Met Glu Pro Gly Thr Glu Ala Met Glu Pro Val Glu Pro
                340                 345                 350
Glu Met Lys Pro Leu Glu Ser Pro Gly Gly Thr Met Ala Pro Gln Gln
            355                 360                 365
Pro Glu Gly Ala Lys Pro Gln Ala Gln Ala Ala Leu Ala Ala Pro Lys
        370                 375                 380
Lys Lys Thr Lys Lys Glu Lys Gln Gln Asp Ala Thr Val Glu Pro Glu
385                 390                 395                 400
Thr Glu Val Val Gly Pro Glu Leu Pro Asp Asp Leu Glu Pro Gln Ala
                405                 410                 415
Ala Pro Thr Ser Thr Lys Lys Lys Lys Lys Lys Glu Arg Gly His
                420                 425                 430
Thr Val Thr Glu Pro Ile Gln Pro Leu Glu Pro Glu Leu Pro Gly Glu
                435                 440                 445
Gly Gln Pro Glu Ala Arg Ala Thr Pro Gly Ser Thr Lys Lys Arg Lys
            450                 455                 460
Lys Gln Ser Gln Glu Ser Arg Met Pro Glu Thr Val Pro Gln Glu Glu
465                 470                 475                 480
Met Pro Gly Pro Pro Leu Asn Ser Glu Ser Gly Glu Glu Ala Pro Thr
                485                 490                 495
Gly Arg Asp Lys Lys Arg Lys Gln Gln Gln Gln Pro Val
                500                 505                 510

<210> SEQ ID NO 2
<211> LENGTH: 3286
<212> TYPE: DNA
<213> ORGANISM: Homo sapiens
<220> FEATURE:
<223> OTHER INFORMATION: Nucleic Acid Sequence of ASE-1

<400> SEQUENCE: 2
aagttctgaa cttgtgaggc atctgggcct ccccagaaga catttaacac agaaagcaca      60
gccctactaa ctagtattct tacctgtctc ttcaagaatt tcagaccaat cgaccgtcct     120
gtctctttaa ggcttaggaa gagcagtgtg gctgcccctt aaggaggcg ttgcaacaaa      180
ccatattgga cagacgatgg gggcgaccca tcgggacccg acgggcctct gactccagca     240
atacagcgaa tcagcggctt tcgggaatac attttttcgga aaaagacttc ttcctcggtt    300
ttctgctctg cacacgttga aattttcccc agttttttcct gcagatcggg agtcgagcaa    360
tgcctacccc cgcgctcccg caccagttgg gcgctcccgg atgatgccct accccttttgg   420
atccacgtgg tctgcaacct ggtgcgagca gcccgggcta caggggttgcc tgaggtgtgg    480
gtcccaggat ggaggagccc caggccggcg atgctgctcg ttctcttgt ccccccaact      540
ttaccgcgaa gccccagcc tcagagtccc ctcgtttctc cttggaggcg ctgacgggtc      600
cagatacgga gctgtggctt attcaggccc ctgcagactt tgccccagaa tgcttcaatg    660
ggcggcatgt gcctctctct ggctcccaga tcgtcaaggg caaattggca ggcaagcggc     720
accgctatcg agtcctcagc agctgtcccc aagctggaga gcgaccctg ctggccccct      780
caacggaggc aggaggtgga ctcacctgtg cctcagcccc ccagggcacc ctaaggatcc     840
ttgagggtcc ccagcaatcc ctgtcaggga gccctctgca gcccatccca gcaagtcccc    900
caccacagat ccctcctggc ctgaggcctc ggttctgtgc ctttgggggc aacccaccag     960
tcacagggcc taggtcagcc ttggccccca acctgctcac ctcagggaag aagaaaaagg   1020
```

-continued

```
agatgcaggt gacagaggcc ccagtcactc aggaggcagt gaatgggcac ggggccctgg    1080
aggtggacat ggctttgggg tcgccagaaa tggatgtgcg gaagaagaag aagaaaaaaa    1140
atcagcagct gaaagaacca gaggcagcag ggcctgtggg gacagagccc acagtggaga    1200
cactggagcc tctgggagtg ctgttcccgt ccaccaccaa gaagaggaag aagcccaaag    1260
ggaaagaaac cttcgagcca gaagacaaga cagtgaagca ggaacagatt aacactgagc    1320
ctctagaaga cacagtcctg tccccgacca aaagagaaa gaggcaaaag gggacggaag    1380
ggatggagcc agaggagggg gtgacagttg agtctcagcc acaggtgaag gtggagccac    1440
tggaggaagc catccctctg cccctacga agaagaggaa aaagaaaag ggacagatgg    1500 caatgatgga gccagggacg gaggcgatgg agccagtgga gccggagatg aagcctctgg    1560
agtccccagg ggggaccatg gcgcctcaac agccagaagg agcgaagcct caggcccagg    1620
cagctctggc agctcccaaa aagaagacga gaaagaaaa acagcaagat gccacagtgg    1680
agccagagac agaggtggtg gggcctgagc tgccggatga ccttgagcct caggcagctc    1740
ccacatccac caagaagaag aagaagaaga agagagagg tcacacagtg actgagccaa    1800
ttcagccact agagcctgaa ctgccagggg agggacagcc tgaagccagg gcaactccgg    1860
gatccaccaa gaagaggaag aagcagagtc aggaaagccg gatgccagag acagtgcccc    1920
aagaggagat gccagggccg ccactgaatt cagagtctgg ggaggaggct cccacaggcc    1980
gggacaagaa gcggaagcag cagcagcagc agcctgtgta gtctgccccc gggaaactga    2040
ggaactaaag aaagctgaag gtgcccacct gggccaccag aagtgacac ccccagaatc    2100 cctccccaga gactgcacca gcgcagccag caggagcctg gcctgggagg acgatttatt    2160
attacactgg gggtttcctt ggcagctggg gtcatcaggg tactttcaag aagggctcgt    2220
gcaggacatc aaacagcctc cgggcctgga tgggagggag aaaaaaatga ggaaccagtc    2280
attaaaggag ctgtttcctg ggtaaatcta gagtgggggtt ttggttcttt attttccct    2340 atacccctcaa gcatttatcc attgagttac aaacaatcca gttacaatct ttttaagtta    2400
ttattattat tattatttt tttttttttg agatggagtc tcgctctgtc gcccaggttg    2460
gagtgcagtg gcgcaatctc ggctcactgc aagctccgcc tcccgggttc acgccattct    2520
cctgcctcag cctcctgagt agctgggact acaggcccct gcccagctaa ttttttgtat    2580
ttttttttag tagagatggg gtttcaccac gttagccagg atggtctcga tctcctgacc    2640
tcctgatgcg cctgcctcag cctcccagtg ctgggattat aggtgtgagc cactgcgcct    2700
ggctaagtta ttattatttt tttgagacag tctcctggtg tcacccaggc tggagtgcag    2760
tggtgtgatc ttggctcact gcaacctccg cctcctgggt tccaacgatt ctcctgcctc    2820
agcctcccga gtagctgggc ctaaaggtgc ccaccactat acccggctaa ttttgtatt    2880 tttagtagag acagggggttt caccatattg gccaggctgg tctcgaactc ctgacctcgt    2940
gatccacctg ccttgacctc ccaaagtgct aggataacag gtgtgagcca ccgcaccctg    3000
ccaagttatt ttaaaatgta ccattattat tgactatagt cacctggttg tgttatcaaa    3060
tagtatgtct tattcattct ttctttgtgt gtgtgtgtgt gtgtgtgtgt gtgtgtggta    3120
cccattaacc ttccccatct ccctgccagc cctaactac cctccccagc tccaggaac    3180 tatccatcca ctcttatctc catgagttca attgttttga ttttagata cacaaataaa    3240 taagaacatg caatgtttgt ctttctgtgc ctggcttatt tcactt                  3286
```

<210> SEQ ID NO 3
<211> LENGTH: 27

```
<212> TYPE: DNA
<213> ORGANISM: Homo sapiens
<220> FEATURE:
<223> OTHER INFORMATION: Sense Primer for ASE-1

<400> SEQUENCE: 3
accgctcgag atggaggagc cccaggc                                                27

<210> SEQ ID NO 4
<211> LENGTH: 21
<212> TYPE: DNA
<213> ORGANISM: Homo sapiens
<220> FEATURE:
<223> OTHER INFORMATION: Anti-Sense Primer to ASE-1

<400> SEQUENCE: 4
cttcttggtg gatccccgag t                                                      21
```